US012050023B2

(12) United States Patent
Wenger et al.

(10) Patent No.: US 12,050,023 B2
(45) Date of Patent: Jul. 30, 2024

(54) SYSTEMS AND METHODS FOR CORRELATING INDOOR AIR QUALITY DATA AND TRENDS TO PATHOGEN REMEDIATION

(71) Applicant: TRANE INTERNATIONAL INC., Davidson, NC (US)

(72) Inventors: Scott Wenger, Mooresville, NC (US); Christos Alkiviadis Polyzois, Bloomington, MN (US)

(73) Assignee: TRANE INTERNATIONAL INC., Davidson, NC (US)

( * ) Notice: Subject to any disclaimer, the term of this patent is extended or adjusted under 35 U.S.C. 154(b) by 821 days.

(21) Appl. No.: 17/085,934

(22) Filed: Oct. 30, 2020

(65) Prior Publication Data

US 2022/0136717 A1   May 5, 2022

(51) Int. Cl.
*F24F 8/10* (2021.01)
*A61L 9/04* (2006.01)
(Continued)

(52) U.S. Cl.
CPC ............... *F24F 8/10* (2021.01); *A61L 9/046* (2013.01); *A61L 9/122* (2013.01); *A61L 9/205* (2013.01);
(Continued)

(58) Field of Classification Search
CPC ... F24F 8/10; F24F 11/52; A61L 9/046; A61L 9/122; A61L 9/205; A61L 2209/111;
(Continued)

(56) References Cited

U.S. PATENT DOCUMENTS 9,593,861 B1    3/2017  Burnett
11,137,163 B2   10/2021 Nasis
(Continued)

FOREIGN PATENT DOCUMENTS

CN    111126875 A   *  5/2020
CN    111126875 A      5/2020
(Continued)

OTHER PUBLICATIONS

EPA, "Biological Pollutant's Impact on Indoor Air Quality", Oct. 16, 2019, web.archive.org/web/20191016065948/https://www.epa.gov/indoor-air-quality-iaq/biological-pollutants-impact-indoor-air-quality (Year: 2019).*

(Continued)

*Primary Examiner* — Catherine T. Rastovski
*Assistant Examiner* — Yossef Korang-Beheshti
(74) *Attorney, Agent, or Firm* — HSML P.C.

(57) ABSTRACT

An indoor air quality (IAQ) control system for a heating, ventilation, air conditioning, and Refrigeration (HVACR) system including an IAQ monitor that collects air quality data from an air quality sensor of an air quality-controlled space; a controller that manages a remediation device of the air quality-controlled space; and an IAQ management server that generates a biological pollutant estimate based on the air quality data using an algorithm that correlates the air quality data to the biological pollutant estimate, and generates a remediation recommendation. Additionally, a control method includes collecting air quality data from an air quality sensor of an air quality-controlled space using an IAQ monitor; managing a remediation device of the air quality-controlled space using a controller; generating a biological pollutant estimate based on the air quality data using an algorithm that correlates the air quality data to the
(Continued)

biological pollutant estimate; and generating a remediation recommendation.

18 Claims, 4 Drawing Sheets

(51) Int. Cl.
| | |
|---|---|
| *A61L 9/12* | (2006.01) |
| *A61L 9/20* | (2006.01) |
| *A61L 9/22* | (2006.01) |
| *B01D 46/00* | (2022.01) |
| *B01D 46/44* | (2006.01) |
| *F24F 8/22* | (2021.01) |
| *F24F 8/24* | (2021.01) |
| *F24F 8/30* | (2021.01) |
| *F24F 11/52* | (2018.01) |
| *F24F 110/64* | (2018.01) |
| *F24F 110/66* | (2018.01) |
| *F24F 110/70* | (2018.01) |
| *F24F 110/72* | (2018.01) |

(52) U.S. Cl.
CPC ............ *A61L 9/22* (2013.01); *B01D 46/0086* (2013.01); *B01D 46/442* (2013.01); *B01D 46/448* (2013.01); *F24F 11/52* (2018.01); *A61L 2209/111* (2013.01); *A61L 2209/14* (2013.01); *A61L 2209/16* (2013.01); *A61L 2209/211* (2013.01); *B01D 2279/35* (2013.01); *B01D 2279/50* (2013.01); *B01D 2279/65* (2013.01); *F24F 8/22* (2021.01); *F24F 8/24* (2021.01); *F24F 8/30* (2021.01); *F24F 2110/64* (2018.01); *F24F 2110/66* (2018.01); *F24F 2110/70* (2018.01); *F24F 2110/72* (2018.01)

(58) Field of Classification Search
CPC ............ A61L 2209/14; A61L 2209/16; A61L 2209/211; B01D 46/0086; B01D 46/442; B01D 46/448; B01D 2279/35; B01D 2279/50

See application file for complete search history.

(56) References Cited

U.S. PATENT DOCUMENTS

| | | |
|---|---|---|
| 2014/0275855 A1 | 9/2014 | LeBoeuf et al. |
| 2016/0209070 A1 | 7/2016 | Hrejsa et al. |
| 2018/0119973 A1* | 5/2018 | Rothman ................. F24F 11/62 |
| 2019/0346417 A1* | 11/2019 | Benefield ................. F24F 11/58 |
| 2020/0103841 A1 | 4/2020 | Pillai et al. |
| 2021/0318010 A1* | 10/2021 | Federspiel ............... F24F 11/30 |

FOREIGN PATENT DOCUMENTS

| | | |
|---|---|---|
| CN | 211013951 U | 7/2020 |
| EP | 1856454 B1 | 6/2017 |
| WO | 2020/039379 A1 | 2/2020 |

OTHER PUBLICATIONS

Patelic, Jovan, "Using IoT Environmental Sensing to Reopen Spaces" White Paper Senseware, 2020 (13 pages).

Extended European Search Report, European Patent Application No. 21205090.0, Dated Mar. 3, 2022 (9 pages).

* cited by examiner

SYSTEMS AND METHODS FOR CORRELATING INDOOR AIR QUALITY DATA AND TRENDS TO PATHOGEN REMEDIATION

FIELD

Described herein are systems and methods directed to heating, ventilation, air conditioning, and refrigeration (HVACR). More particularly, systems and methods directed to correlating biological pollutant loads with indoor air quality data and trends of inorganic, volatile organic compound, and particulate matter air pollutants, and estimating biological pollutant or pathogen remediation efficacy.

BACKGROUND

Currently, the world is experiencing a global pandemic at levels unseen since 1919. Unlike the pandemic in 1919, building owners and operators (commercial, industrial and residential) have different challenges to address the pathogen spread, for example, more complicated building and space design, an increased populous and densities of people, the increased movement of people worldwide and the general increasing interconnectedness of people worldwide, as well as the technologies associated with accommodating these complications and increases. Building owners and operators turn to building policies, procedures, and operations and use technology to recommend appropriate remediation methods and systems to kill pathogens and keep air clean. The efficacy of these building policies, procedures, and operations can be validated by a reduction of biological, microbe, or pathogen load. While continuously sensing digital solutions for inorganic, volatile organic compound, and particulate matter air pollutants can be cost-effective for HVACR systems, continuously sensing digital solutions for directly monitoring biological, microbe, or pathogen load are still expensive and likely cost-prohibitive for building owners and operators to validate the reduction of biological, microbe, or pathogen load.

SUMMARY

It is desirable for building operators to continuously monitor the biological, microbe, or pathogen load in the building and effectuate appropriate remediation actions to kill pathogens and keep air clean. However, continuously sensing digital solutions for directly monitoring biological, microbe, or pathogen load that are engineered for laboratories or clinical environments are cost-prohibitive for more general-purpose buildings such as office buildings, condominiums, and apartment complexes. Thus, systems and methods are desirable for estimating biological, microbe, or pathogen load from indoor air quality data and trends of inorganic, volatile organic compound, and particulate matter air pollutants.

According to an embodiment, an indoor air quality (IAQ) control system for a heating, ventilation, air conditioning, and Refrigeration (HVACR) system, includes an IAQ monitor that is configured to collect air quality data from an air quality sensor of an air quality-controlled space, a controller that is configured to manage a remediation device of the air quality-controlled space, and an IAQ management server that is configured to generate a biological pollutant estimate based on the air quality data using an algorithm that correlates the air quality data to the biological pollutant estimate. The IAQ control system is configured to generate a remediation recommendation based on the biological pollutant estimate.

The IAQ management server can be further configured to control the remediation device directly or via the controller according to the remediation recommendation if the remediation recommendation can be executed by the remediation device; or recommend installing another remediation device appropriate for a type of pollutant being remediated if the remediation recommendation cannot be executed by the remediation device.

The IAQ management server can be further configured to estimate efficacy of the remediation of a biological pollutant using a rate of change of the air quality data or a change in the air quality data before and after the remediation recommendation is executed.

The air quality data collected by the IAQ monitor can include a measurement of carbon dioxide, a volatile organic compound, a particulate matter, temperature, humidity, carbon monoxide, nitrogen dioxide, or sulfur dioxide.

The algorithm can be further configured to be updated by one or more of user feedback, a remediation response outcome, or an updated prediction model generated from empirical or simulated data.

The algorithm can be further configured to generate the biological pollutant estimate using ambient air quality data.

The remediation device can include one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

The remediation device can be controllable by the controller, by a secondary controller, or by a user.

The IAQ management server can be further configured to deliver the remediation recommendation to a display on the controller, the IAQ monitor, or a user device.

The IAQ management server can be further configured to generate the remediation recommendation based on a trend in the air quality data over time.

In another embodiment, an indoor air quality (IAQ) method for a heating, ventilation, air conditioning, and Refrigeration (HVACR) system includes collecting air quality data from an air quality sensor of an air quality-controlled space using an IAQ monitor, managing a remediation device of the air quality-controlled space using a controller, generating a biological pollutant estimate based on the air quality data using an algorithm that correlates the air quality data to the biological pollutant estimate, and generating a remediation recommendation based on the biological pollutant estimate.

The method can further comprise controlling the remediation device directly or via the controller according to the remediation recommendation if the remediation recommendation can be executed by the remediation device; or recommending installing another remediation device appropriate for a type of pollutant being remediated if the remediation recommendation cannot be executed by the remediation device.

The method can be further comprising estimating efficacy of the remediation of a biological pollutant using a rate of change of the air quality data or a change in the air quality data before and after the remediation recommendation is executed.

The air quality data collected by the IAQ monitor can include a measurement of carbon dioxide, a volatile organic compound, a particulate matter, temperature, humidity, carbon monoxide, nitrogen dioxide, or sulfur dioxide.

The algorithm can be updated by user feedback, a remediation response outcome, or an updated prediction model generated from empirical or simulated data.

The algorithm can be further configured to generate the biological pollutant estimate using ambient air quality data.

The remediation device can include one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

The remediation device is controllable by the controller, by a secondary controller, or by a user.

The method can further comprise delivering the remediation recommendation to a display of the controller, the IAQ monitor, or a user device.

The method can further comprise generating the remediation recommendation based on a trend in the air quality data over time.

BRIEF DESCRIPTION OF THE DRAWINGS

References are made to the accompanying drawings that form a part of this disclosure, and which illustrate embodiments in which the systems and methods described in this Specification can be practiced.

Like reference numbers represent like parts throughout.

DETAILED DESCRIPTION

Figure 1:
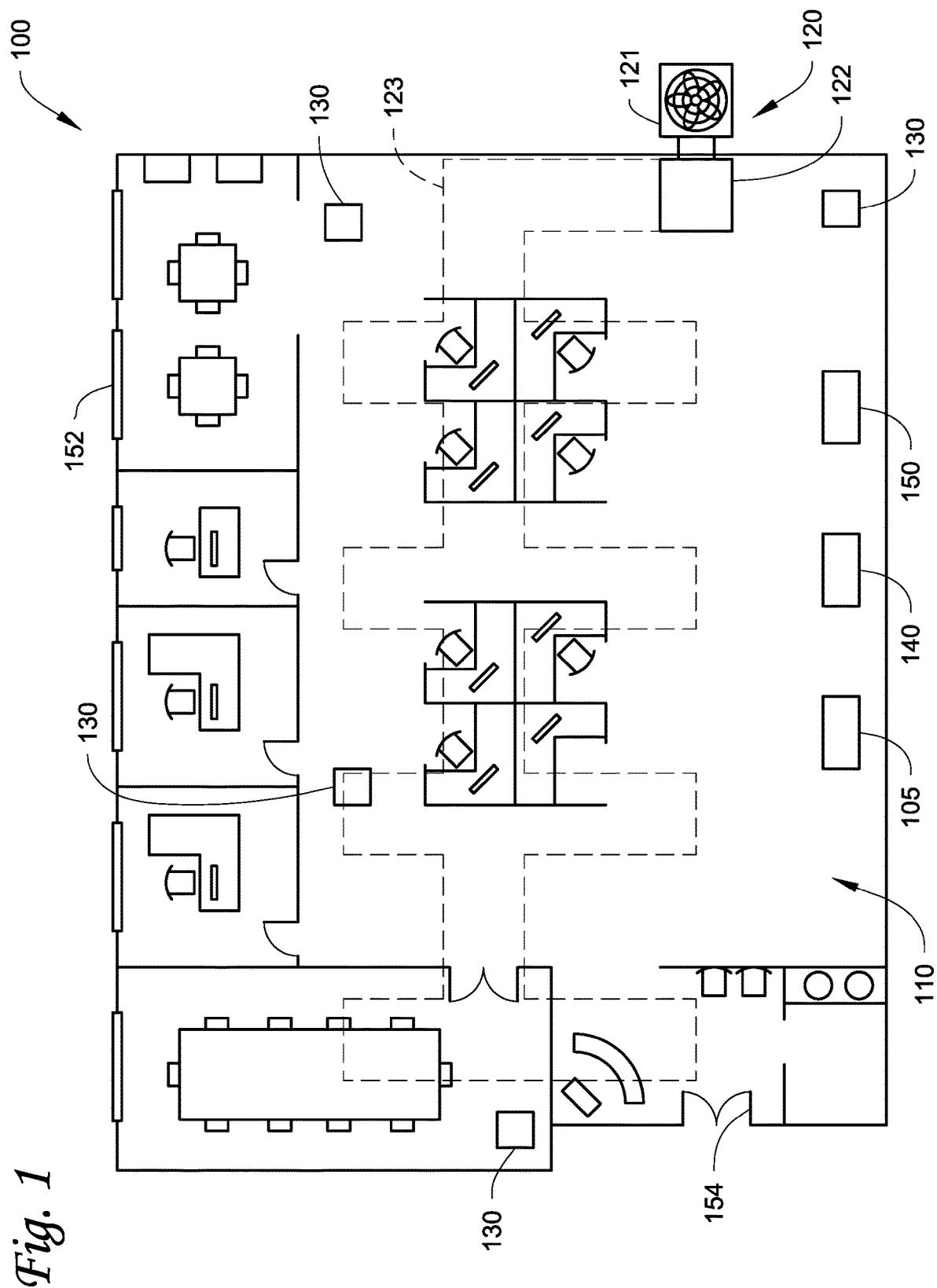
FIG. 1 is a schematic view of a facility serviced by an HCACR system, according to an embodiment.

This disclosure relates generally to systems and methods directed to heating, ventilation, air conditioning, and refrigeration (HVACR). More specifically, this disclosure relates to systems and methods that correlate air quality data in a prediction model to effectuate appropriate remediation actions and estimate remediation efficacy, without dedicated indoor pathogen detectors.

As defined herein, the term "software" can refer to prescribed rules to operate a computer. Examples of software can include: software; code segments; instructions; applets; pre-compiled code; compiled code; interpreted code; computer programs; and programmed logic, and the like. In this description, the terms "software" and "code" can be applicable to software, firmware, or a combination of software and firmware, and the like.

As defined herein, the term "computer-readable medium" can refer to any storage device used for storing data accessible by a computer. Examples of a computer-readable medium can include: a magnetic hard disk; a floppy disk; an optical disk, such as a CD-ROM and a DVD; a magnetic tape; a flash removable memory; a memory chip; and/or other types of media that can store machine-readable instructions thereon, and the like. As defined herein, the term "non-transitory" computer-readable medium includes any computer-readable medium, with the sole exception being a transitory, propagating signal, and the like.

As defined herein, the term "computer system" can refer to a system having one or more computers, where each computer can include a computer-readable medium embodying software to operate the computer. Examples of a computer system can include: a distributed computer system for processing information via computer systems linked by a network; two or more computer systems connected together via a network for transmitting and/or receiving information between the computer systems; and one or more apparatuses and/or one or more systems that can accept data, can process data in accordance with one or more stored software programs, can generate results, and typically can include input, output, storage, arithmetic, logic, and control units; and the like.

As defined herein, the term "network" can refer to a number of computers and associated devices that can be connected by communication facilities. A network can involve permanent connections such as cables or temporary connections such as those made through telephone or other communication links. A network can further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network can include: an internet, such as the Internet; an intranet; a local area network (LAN); a wide area network (WAN); and a combination of networks, such as an internet and an intranet. Exemplary networks can operate with any of a number of protocols, such as Internet protocol (IP), asynchronous transfer mode (ATM), and/or synchronous optical network (SONET), user datagram protocol (UDP), IEEE 802.x, etc.

As defined herein, the term "indoor air quality" or "IAQ" can refer to the quality of air that is being circulated and/or recirculated inside of a facility (such as a building, an installation, or any suitable enclosed area, etc.) by using, e.g., an HVACR system or the like. IAQ can be represented by air quality data. The air quality data can include, for example, quantities of inorganic air pollutants such as carbon dioxide, carbon monoxide, nitrogen dioxide, sulfur dioxide. The air quality data can include, for example, amounts of volatile organic compounds, particulate matter, or the like. The air quality data can also include temperature, humidity, or location data, or the like.

Particular embodiments of the present disclosure are described herein with reference to the accompanying drawings; however, it is to be understood that the disclosed embodiments are merely examples of the disclosure, which can be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Additionally, the present disclosure can be described herein in terms of functional block components, code listings, optional selections, page displays, and various processing steps. It should be appreciated that such functional blocks can be realized by any number of hardware and/or software components configured to perform the specified functions. For example, the present disclosure can employ various integrated circuit components, e.g., memory elements, processing elements, logic elements, look-up tables, and the like, which can carry out a variety of functions under the control of one or more microprocessors or other control devices.

Further, it should be noted that the present disclosure can employ any number of conventional techniques for data transmission, signaling, data processing, network control, and the like. It should be appreciated that the particular implementations shown and described herein are illustrative of the disclosure and its best mode and are not intended to otherwise limit the scope of the present disclosure in any way. Examples are presented herein which can include sample data items (e.g., names, dates, etc.) which are intended as examples and are not to be construed as limiting. Indeed, for the sake of brevity, conventional data networking, application development and other functional aspects of the systems (and components of the individual operating components of the systems) cannot be described in detail herein. Furthermore, the connecting lines shown in the various figures contained herein are intended to represent example functional relationships and/or physical or virtual couplings between the various elements. It should be noted that many alternative or additional functional relationships or physical or virtual connections can be present in a practical electronic data communications system.

As will be appreciated by one of ordinary skill in the art, the present disclosure can be embodied as a method, a data processing system, a device for data processing, and/or a computer program product. Accordingly, the present disclosure can take the form of an entirely software embodiment, an entirely hardware embodiment, or an embodiment combining aspects of both software and hardware. Furthermore, the present disclosure can take the form of a computer program product on a computer-readable storage medium having computer-readable program code means embodied in the storage medium. Any suitable computer-readable storage medium can be utilized, such as, for example, hard disks, CD-ROM, DVD-ROM, optical storage devices, magnetic storage devices, semiconductor storage devices (e.g., USB thumb drives), and/or the like.

The present disclosure is described below with reference to block diagrams and flowchart illustrations of methods, apparatus (e.g., systems), and computer program products according to various aspects of the disclosure. It will be understood that each functional block of the block diagrams and the flowchart illustrations, and combinations of functional blocks in the block diagrams and flowchart illustrations, respectively, can be implemented by computer program instructions. These computer program instructions can be loaded onto a general-purpose computer, special purpose computer, mobile device, or other programmable data processing apparatus to produce a machine, such that the instructions that execute on the computer or other programmable data processing apparatus create means for implementing the functions specified in the flowchart block or blocks.

These computer program instructions can also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems that perform the specified functions or steps, or suitable combinations of special purpose hardware and computer instructions.

One skilled in the art will also appreciate that, for security reasons, any databases, systems, or components of the present disclosure can have any combination of databases or components at a single location or at multiple locations, wherein each database or system includes any of various suitable security features, such as firewalls, access codes, encryption, de-encryption, compression, decompression, and/or the like.

FIG. 1 is a schematic view of a facility serviced by an HCACR system, according to an embodiment. As shown in FIG. 1, a facility 100 can include an IAQ monitor 105, an air quality-controlled space 110, a HVACR system 120, a plurality of sensors 130 connected to the IAQ monitor 105, a controller 140 that manages a remediation device 150.

The facility 100 can be an office building, a condominium, an apartment complex, a factory, a public space, or the like, where continuously sensing digital solutions for directly monitoring biological, microbe, pathogen load (or alternatively referred to as biological pollutant load) can be cost-prohibitive.

The IAQ monitor 105 can provide a remediation recommendation to a user to take appropriate remediation action. The remediation recommendation can be provided through a display attached to the IAQ monitor 105. Alternatively, the remediation recommendation can be delivered through a screen, an application, a dashboard accessible by an internet browser, or the like.

The IAQ monitor 105 can calculate qualitative or quantitative feedback on the current air quality based on a current reading of air quality data collected from sensors 130. The feedback on current air quality can be a score, a letter grade, an assessment (e.g., good, normal, or bad), or the like. The IAQ monitor 105 can be a mobile device, a software application on a mobile device, a dashboard accessible through a web browser, or the like.

The air quality-controlled space 110 can include one or more enclosed spaces or areas with one or more occupancies including, for example, a conference room, a cubicle area, a breakroom, an office suite, a floor of a building, a building, a production floor, or the like.

The HVACR system 120 can include an outdoor unit 121, an indoor unit 122, and ducts 123. The indoor unit 122 can intake indoor air from and deliver conditioned air to specific areas within the air quality-controlled space 110 using the ducts 123.

The sensors 130 in FIG. 1 are air quality sensors that generate air quality data. The air quality data can include air quality parameters measured by sensors 130 such as quantities of carbon dioxide, carbon monoxide, nitrogen dioxide, sulfur dioxide, or the like. The air quality data can also include other parameters such as quantities of one or more volatile organic compounds, quantities of particulate matter, temperature, humidity, location data, or the like. In an embodiment, the quantities that can be quantities that are correlated with a quantity of a biological pollutant such as a pathogen.

It is also appreciated that the sensors 130 can be connected over a network with or integrated into other devices such as the IAQ monitor 105, the controller 140, the remediation device 150, the indoor unit 122, and the like.

The controller 140 of FIG. 1 manages the remediation device 150 directly or over a network. The controller 140 is illustrated to be positioned near a wall within the air quality-controlled space 110. It is appreciated that the controller 140 can be connected over a network with or integrated into other devices such as the IAQ monitor 105, one or more of the sensors 130, the remediation device 150, the indoor unit 122, and the like.

In another embodiment, the controller 140 can be included in a mobile device, a software application on a mobile device, a dashboard accessible through a web browser, or the like.

The remediation device 150 reduces air pollutants from the air quality controlled space. The reduction can be achieved by adhesion, filtration, neutralization through physical, electrical, or chemical methods, replacement of more polluted air with less polluted air, or the like. For example, remediation device 150 can include one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or ventilation such as a ventilation system, a door or a window of the air quality controlled space. The reduction in pollutants can include reduction in biological pollutants such as pathogens.

The remediation device 150 can be a connected device, or a conventional device not connected to the controller 140. A connected device can connect directly to the controller 140 over a network such as a wired or wireless network. A conventional device can be a fan, a window 152, a door 154 that is not directly controllable by the controller 140 over a network. It is appreciated that the remediation device 150 can be a conventional device controlled by a secondary controller that is connected to the controller 140 over a network. The secondary controller can be a connected switch that communicates with the controller 140 over a network. The controller 140 can further be configured to control power sources, switches, or the like such that it can control the activity of conventional devices.

According to one embodiment, the connected switch can be preprogrammed to communicate with the controller 140 over a network. The connected switch can be designed to retrofit to a conventional device. The connected devices or switches can alternatively be referred to as a smart device or smart switch. The preprogramming can include embedding one or more QR codes that can be scanned by a camera. The QR codes can be located on the devices, the user manual, the packaging, or the like. The QR codes can include MAC addresses, serial numbers, or other wireless setup parameters. The QR codes can be one non-limiting example of a device identifier for the device that is being connected to the connected switch. In another embodiment, the smart switches or smart devices can include short-range communication devices, such as a BLUETOOTH® beacon, for example to communicate with the controller 140 and/or to receive device identifiers from devices connected to the connected switch.

Figure 2:
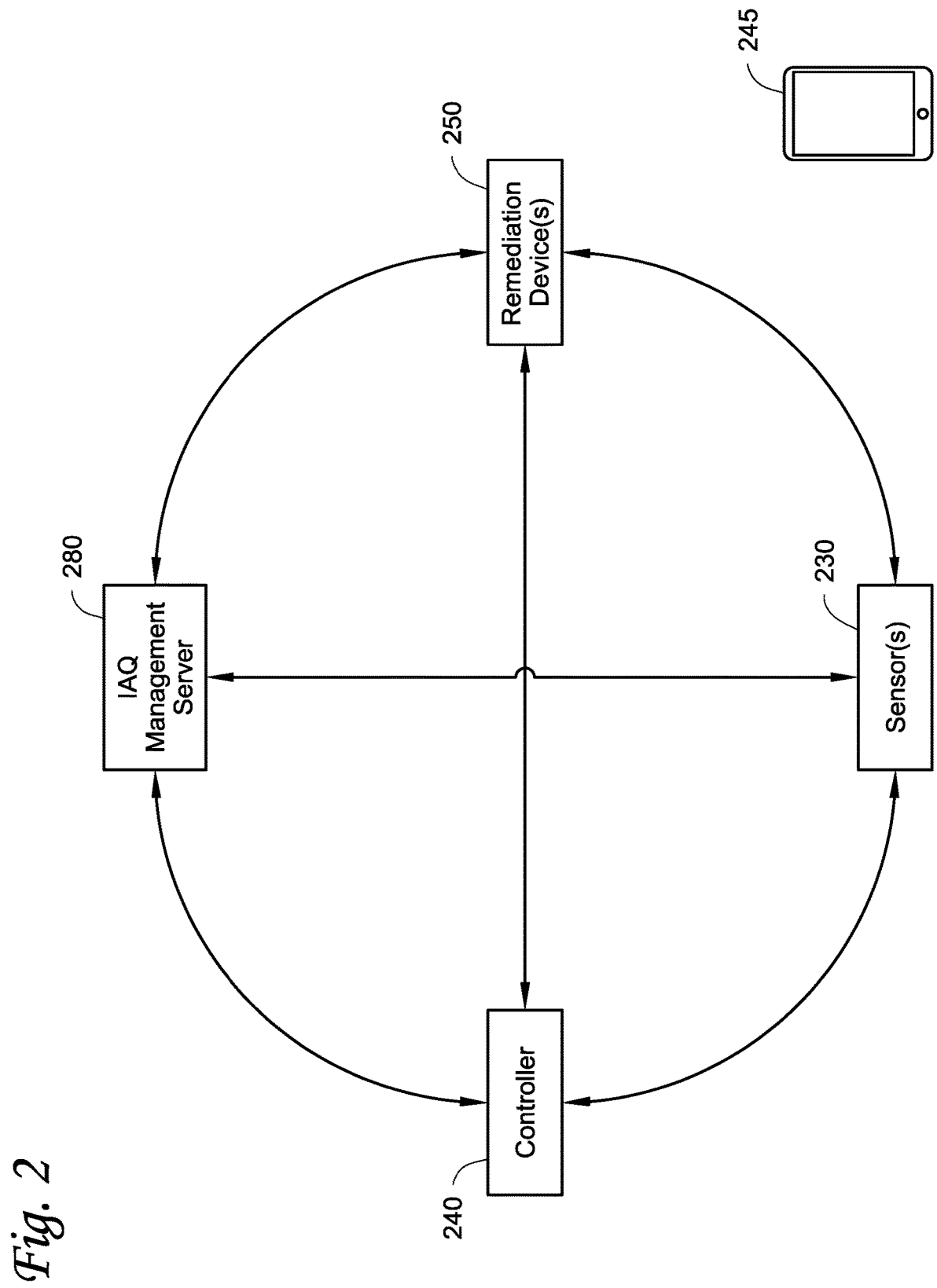
FIG. 2 is a schematic view of a system for managing air quality control devices according to an embodiment.

FIG. 2 is a schematic view of a system for managing air quality control devices according to an embodiment. As shown in FIG. 2, the air quality control devices include sensors 230, a controller 240, a remediation device 250, and an IAQ management server 280 directly or indirectly connected with one another over a network. It is appreciated that each and every connection among the components illustrated in FIG. 2 is not required.

In another embodiment, the system comprises a user device 245 that acts as a conduit that connects to one or more of the sensors 230, the controller 240, the remediation device 250, and the IAQ management server 280 over a network.

In yet another embodiment, the user device 245, the controller 240, and the IAQ management server 280 can be integrated into a single device.

The sensors 230 collect air quality data and transmit the collected air quality data to other devices for further processing. For example, the air quality data can be transmitted to the controller 240. The controller 240 can process the air quality data according to an algorithm that further transmits the air quality data to the IAQ management server 280 for further processing, instruct the remediation device 250 to execute a remediation action, or both. The sensors 230 can be, for example, the sensors 130 shown in FIG. 1 and described above.

The remediation device 250 can receive the air quality data from the sensors 230, and an internal controller of the remediation device 250 can trigger one or more remediation actions according to an algorithm of the internal controller and the air quality data received.

The internal controller can trigger the remediation device 250 to execute a remediation action when an air quality parameter reaches a threshold value. In one embodiment, the threshold value is predetermined, for example, by a manufacturer or a servicer according to industry standards such as: WELL BUILDING STANDARD® and RESET®, or government standards such as those promulgated by the Occupational Safety and Health Administration (OSHA), the United States Environmental Protection Agency (EPA), or the World Health Organization (WHO). In another embodiment, the threshold value can be determined by the user according to the needs of the occupants.

The predetermined threshold value can be adjusted by a user. The system can provide recommendations for the user to adjust the threshold value through a user interface of a communication device. The communication device can be integrated into one or more of the sensor 230, the user device 245, the controller 240, and the server 280. The communication device can be a visual feedback output device, such as a monitor, a television, a display, and the like.

The user interface can include selectable options to adjust the threshold value and/or adjust an aggressiveness in remediation, such as the frequency and/or intensity of the remediation action. The user interface can include additional information about potential benefits or consequences of adjusting the threshold value and/or the intensity. For example, the additional information can include one or more of a correlation between the intensity of the remediation and the energy consumption, the noise generation, and/or the time required to complete the remediation action performed by the one or more remediation devices. For example, the user interface can inform the user that a higher intensity setting of a remediation action can consume more energy, create more noise, and complete within a shortened period of time.

In one embodiment, the remediation device can be triggered proactively before an air quality parameter reaches a predetermined threshold. The proactive triggering can be determined by a trend of air quality data recorded over time. The proactive triggering can be determined by factors or patterns recognized and/or updated by a machine learning algorithm or artificial intelligence (AI). The remediation device 250 can be, for example, the remediation device 150 shown in FIG. 1 and described above.

The remediation device 250 can maintain a remediation record to be transmitted to the controller 240 or the IAQ management server 280 for further processing. In another embodiment, the controller 240 or the server 280 can maintain the remediation record. In one embodiment, the further processing of the remediation record can be calculating efficacy of a remediation action by the IAQ management server 280, updating a prediction model or algorithm of the IAQ management server 280, or the like. The remediation device 250 can be, for example, the remediation device 150 shown in FIG. 1 and described above.

The server 280 includes an algorithm that uses the air quality data from the sensors 230 as inputs, and uses a prediction model generated from experimental or simulated data to estimate a biological pollutant load in an air quality controlled space where the system is deployed. The server 280 can generate a remediation recommendation according to the type and severity of an air pollutant. The air pollutant can be a biological pollutant.

The server 280 can deliver the remediation recommendation to the controller 240, control the remediation device 250 directly to execute a remediation action, or both.

The server 280 can generate a second biological pollutant load estimate after the remediation action is completed. The server 280 can compare the second biological pollutant load estimate with an initial biological pollutant estimate to determine a projected reduction value indicative of pathogen remediation efficacy. The projected reduction value can be generated from experimental or simulated data.

In one embodiment, the server 280 can incorporate ambient air quality data as inputs into the algorithm to estimate the biological pollutant load, to generate the remediation recommendation, and to calculate the pathogen remediation efficacy. In another embodiment, the server 280 can incorporate efficacy of air quality parameter monitored by the sensors 230 as inputs into the algorithm to calculate the remediation efficacy of the biological pollutant.

Figure 3:
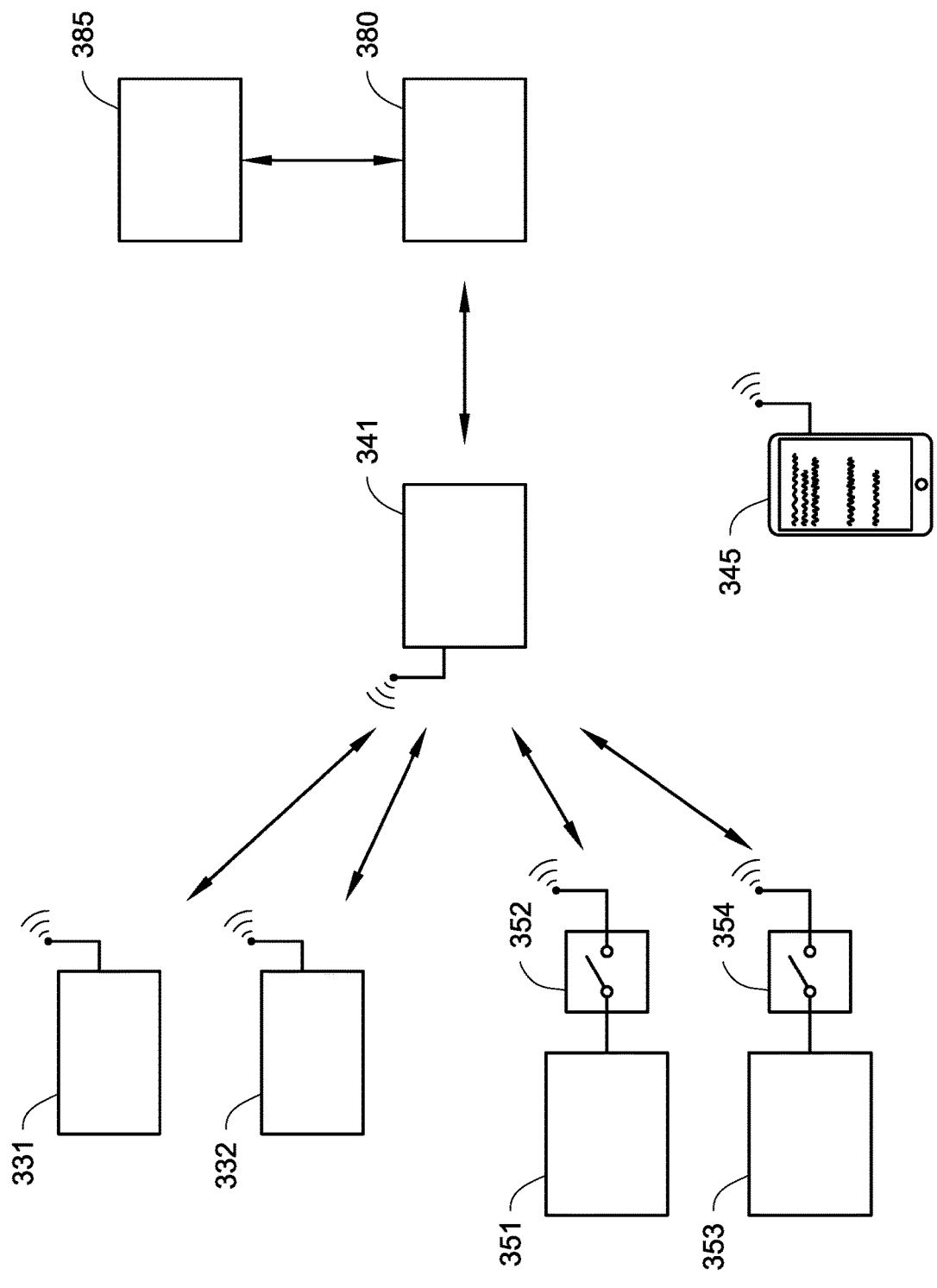
FIG. 3 is a schematic view of a control system for air quality control devices according to an embodiment.

FIG. 3 is a schematic view of a control system for air quality control devices in an HVACR system, according to an embodiment. As shown in FIG. 3, sensors 331 and 332, remediation devices 351 and 353, and an IAQ management server 380 are connected through a controller 341 over a wireless network. The IAQ management server 380 is further communicated with an ambient air quality database 385.

It is appreciated that the connection between devices in FIG. 3 can be connected over any suitable network. It is also appreciated that, although FIG. 3 shows two IAQ monitors, the disclosed system can be configured to include only one IAQ monitor or more than two IAQ monitors.

The sensors 331 and 332 are respectively integrated into first and second IAQ monitors. The sensors 331 and 332 collect air quality data of the air quality-conditioned space. It is appreciated that the first and the second IAQ monitors can be positioned in the same area within an air quality-controlled space. The sensors 331 and 332 can be, for example, the sensors 230 shown in FIG. 2 and described above.

The first and second IAQ monitors can be positioned in different areas within the air quality-controlled space. The air quality data collected can be labeled to identify the room from which the air quality data are collected. The air quality data collected can be time stamped.

The controller 341 can include a display (not shown). A user device 345 can also be included in the system performing the same functions as the controller 341. The controller 341 can be, for example, the controller 240 shown in FIG. 2 and described above.

The remediation devices 351 and 353 can be controlled by the controller 341 through connected switches 352 and 354, respectively. The connected switches 352 and 354 can be connected to the controller 341 over a network such as a wired or wireless network. The remediation devices 351 and 353 can be, for example, the remediation device 250 shown in FIG. 2 and described above.

The server 380 receives air quality data from the sensors 331 and 332 over a network through the controller 341. The server 380 processes the air quality data to estimate a biological pollutant load. Server 380 can further generate a remediation recommendation and transmit the remediation recommendation to the controller 341. The controller 341 then can instruct the connected switch 352, 354, or both to control the remediation device 351, 353, or both, and execute a remediation action according to the remediation recommendation from the server 380.

The server 380 can acquire ambient air quality data from the ambient are quality database 385 to supplement the inputs to its algorithm.

It is appreciated that the function of the server can be performed by the user device 345. The user device 345 can replace the server 380, replicate the functions of the server 380, or extend the functions of the server 380. The server 380 can be, for example, the server 280 shown in FIG. 2 and described above.

Figure 4:
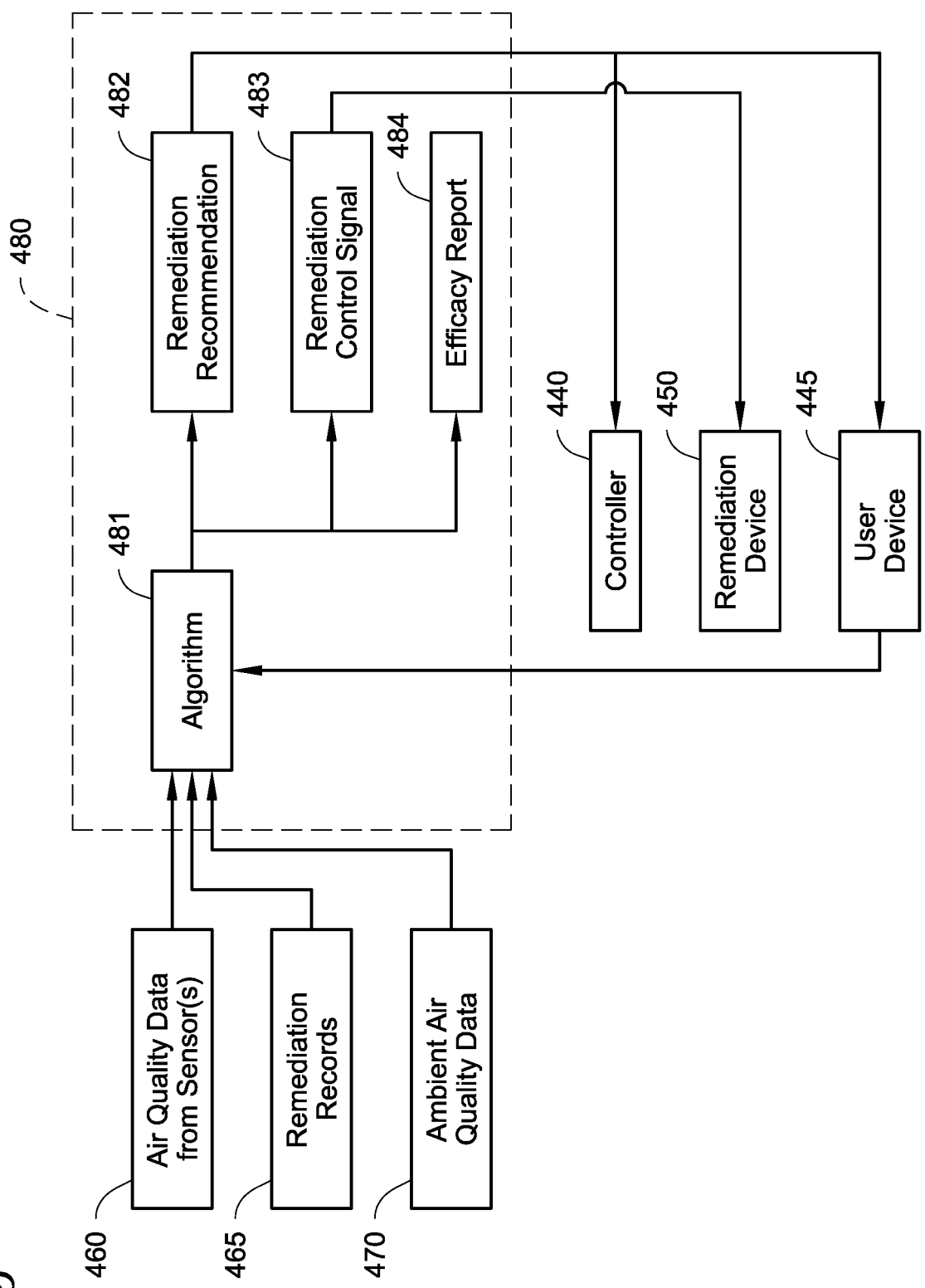
FIG. 4 is a block diagram representing controls for air quality control devices according to an embodiment.

FIG. 4 is a block diagram representing controls for air quality control devices in an HVACR system, according to an embodiment. As shown in FIG. 4, an algorithm 481 is used by a server 480 to estimate biological pollutant load from air quality data collected by sensors. The algorithm 481 receives air quality data 460 from the sensors of an air quality-controlled space as inputs. The algorithm 481 can also receive remediation records 465 from a controller or remediation devices connected to the server 480. The algorithm 481 can also receive the remediation record 465 maintained by the server 480.

The algorithm 481 can also receive ambient air quality data 470. The ambient air quality data 470 can include the air quality data outside of the air quality-controlled space. The ambient air quality can affect the efficacy of remediation actions that introduce air from the ambient environment relevant to the air quality-controlled space. The ambient environment can be an indoor space or an outdoor space. For example, an indoor space ambient environment can be a public area of an office building while the air quality-controlled space can be an office suite within the office building. The ambient air quality data 470 can include parameters such as a quantity of carbon dioxide, a quantity of one or more volatile organic compounds, quantities of particulate matter, temperature, humidity, a quantity of carbon monoxide, a quantity of nitrogen dioxide, and/or a quantity of sulfur dioxide. The measurement can be a concentration, a flow rate, a count, or the like. In an embodiment, the ambient air quality data 470 can include biological pollutant data relevant to the air quality-controlled space.

The algorithm 481 includes a prediction model constructed from experimental or simulated data that correlates air quality data as inputs with a biological pollutant load as an output. The input data of the prediction model can also include ambient air quality data as inputs.

The server 480 generates a remediation recommendation that can include utilization of a remediation device appropriate for remediating an air quality issue of the air quality-controlled space. A non-limiting example of an air quality issue is when a biological pollutant load estimated from the air quality data is higher than a predetermined value. The remediation recommendation from the server 480 is transmitted over a network to a controller 440, a user device 445, or both. The remediation recommendation can be transmitted as a control signal 483 to directly instruct a remediation device 450 to perform a remediation action.

According to one embodiment, the controller 440, the user device 445, or both can include a screen to display the remediation recommendation from the server 480. The remediation recommendation can be translated by the controller 440, the user device 445, or both into layman terms so that a user not familiar with air quality control technologies can understand the air quality problem and the appropriate remediation action to mitigate the particular kind of air quality problem.

The server 480 can generate a remediation recommendation for a recurring air quality problem based on a trend in air quality data and generate a remediation recommendation in anticipation of a drop in air quality parameter, and thus eliminate or reduce the recurring air quality problem.

The server 480 can generate a remediation recommendation based on a trend in air quality data or in efficacy. For example, the efficacy of an air filtering device can decrease over time. The server 480 detects this trend and generates a recommendation to clean or replace a filter of the air filtering device by an expected time or date when the efficacy is expected to fall below a threshold value.

The server 480 can also calculate efficacy of a remediation action by comparing the air quality data of the air quality-controlled space over time. The efficacy can be a difference between a reduction of an air pollutant monitored by the air quality sensor after a remediation action, compared to a predicted reduction of the air pollutant without the remediation action. The predicted reduction of the air pollutant can be based on experimental or simulated data.

In an embodiment, the air pollutant can be a biological pollutant, and the reduction of the biological pollutant can be estimated from the air quality data before and after the remediation action using the algorithm 481. The server 480 can generate an efficacy report of the air pollutant remediation action and transmit the report to the user device 445, the controller 440, or both. In another embodiment, a change of a pollutant load can be estimated from the air quality data before and after a remediation action. The pollutant can be any type of pollutant measured economically and/or continuously by one or more air quality sensors. The change in pollutant load can be included in an efficacy report 484 for the air pollutant remediation action. The efficacy report 484 can be transmitted to the user device 445, the controller 440, or both. In an embodiment, the efficacy report 484 can include an equivalent ventilation time by correlating the change of the pollutant load to an equivalent time period of ventilation with ambient air.

The algorithm 481 can be updated based on feedback from the user device 445 generated by a user. Additionally, the algorithm 481 can be updated by comparing an air quality parameter predicted to be after a remediation action and an air quality data measured by sensors after the remediation action. The algorithm 481 of the server 480 can also be updated by an updated prediction model generated from updated experimental or simulated data. The controller 440, the remediation device 450, the user device 445, and server 480 can respectively be, for example, the controller 341, the remediation devices 351 and 353, the user device 345, and the server 380 shown in FIG. 3 and described above.

The prediction model can be generated and updated by artificial intelligence (AI), machine learning, or the like. The AI prediction model can be trained with one or more data sets of air quality parameters that can be continuously and/or economically measured by one or more air quality sensors measuring one or more of the air quality parameters. The data set can further include, for example, one or more of the location of the air quality sensors and the remediation devices. The location can be in relation to the position of the sensor within the air quality-controlled space. The data set can include identification of outlier or anomaly events for correction. For example, the outlier or anomaly event can include, as non-limiting examples, a spikes in total volatile organic compounds due to hand sanitizer uses by occupants or alcoholic beverages near the air quality sensors, or any other event capable of producing an outlier in one or more of the air quality parameters. According to one embodiment, the AI prediction model can be algorithm 481. The prediction model can be a dynamic model that is updated using data obtained from observation or experimentation regarding the effectiveness of remediation within a space. In an embodiment, the dynamic model can be updated regularly and/or according to events that may change the airflow or other conditions within the space.

The air quality parameters that can be continuously and/or economically measured include one or more measurements of carbon dioxide, a volatile organic compound, a particulate matter, temperature, humidity, carbon monoxide, nitrogen dioxide, or sulfur dioxide. The air quality parameters continuously and/or economically measured can further include air quality data acquired from a database, such as a database with the ambient air quality parameters. Other air quality parameters, which can optionally not be monitored by continuous air quality sensors, can be a biological pollutant load, such as a virus load, a bacteria load, a pathogen load, or the like.

The system can further include a program for guiding a user to conduct an efficacy demonstration of one or more remediation devices performing one or more remediation actions. The guiding can be delivered through a communication device.

The communication device can be part of one or more of the sensor 230, the user device 245, the controller 240, and the server 280. According to one embodiment, the communication device can be a visual feedback output device, such as a monitor, a television, a display, and the like.

The efficacy demonstration can be a controlled experiment conducted by introducing a predetermined air pollutant into the air quality controlled space followed by executing a corresponding remediation action using one or more remediation devices. For example, the predetermined air pollutant can be ethanol, aerosol sunscreen, hairspray, or the like. In an embodiment, the predetermined air pollutant can be any suitable pollutant affected by the remediation devices, such as, for example, oxidizable compounds such as VOCs where the remediation devices act by providing hydrogen peroxide or function based on oxidization, such as photocatalytic oxidation. In an embodiment, the predetermined air pollutant can be any suitable proxy for the effects of remediation actions on biological pollutants such as pathogens. For example, the predetermined air pollutant can be a pollutant affected by the remediation actions in a similar manner to biological pollutants, for example a compound oxidized by the remediation action. The efficacy demonstration can be guiding a user to introduce a predetermined amount of the predetermined air pollutant. The predetermined amount can be an equivalent amount of the predetermined air pollutant released by a canister of the predetermined air pollutant spraying over a predetermined amount of time. For example, the predetermined amount of time maybe ten seconds. In an embodiment, the efficacy demonstration can be used to generate or validate a model of remediation effectiveness within a particular space, such as one or more rooms, floors, or buildings including an HVACR system and remediation devices.

The efficacy demonstration can record the air quality parameters before and after the remediation action for calculating efficacy of the remediation action. The calculation can further estimate efficacy of biological pollutant remediation using a correlation between the predetermined air pollutant and a biological pollutant to show the user what the biological pollutant remediation efficacy would be for the performed remediation action. The system can compare the calculated efficacy to a theoretical or historical efficacy to identify a problem with a remediation device and to transmit an alert to the user through the user interface of the communication device. For example, the problem can be a dirty filter that needs to be cleaned or replaced.

According to an embodiment, an efficacy demonstration can include validating an efficacy of a pathogen remediation to show the safety of air quality controlled space. The validation can be conducted using a reagent as a proxy which can be feasibly measured in a HVACR system of a general purpose building. The proxy can be correlated using experimental or simulated data to predict the actual remediation of biological pathogen in an air quality controlled space. For example, the reagent or proxy can be a predetermined quantity of a reagent that is reactive with hydrogen peroxide. The hydrogen peroxide can be generated by remediation devices. The concentration of the reagent or of hydrogen peroxide in the air quality controlled space can be correlated with a reduction of pathogen using the experimental or simulated data regarding consumption of the reagent and/or hydrogen peroxide. The correlation can further include a concentration of hydrogen peroxide over time for calculating the efficacy of the pathogen remediation. According to another embodiment, the reagent as a proxy can be a compound reactive with UV light, a particle that can be captured by a filter, or any other suitable proxy for a biological pollutant that can be acted on by a remediation device.

The system can guide the user to enter location information into the system through a user interface. The location information can be the location of the air quality controlled space in relation to a geographical area, such as zip code, a street address, a coordinate on a map, or the like. The location information can include the location of the air quality monitor, the sensors, the user device, and the remediation devices in relation to the air quality controlled space, such as a first conference room, a second conference room, a living room, a front desk area, a breakroom area, a floor level, a cubicle area, or the like. The location information can be used to generate and update the algorithm 481. The location information can further be used in the efficacy demonstration to generate and update the correlation between the pathogen and the reagent as a proxy feasibly measurable in a HVACR system in a general purpose building. For example, the correlation can be tailored to the air quality controlled space based on the location of the remediation devices. Further, the efficacy of the remediation can be estimated based on the location of the sensor that is positioned in a particular room. For example, the remediation device is located in the living room, while the bedroom is adjacent to the living room. The pathogen remediation efficacy of the living room, because it is closer to the remediation device, can be higher than the remediation efficacy of the bedroom. The correlation can incorporate the location information of the remediation device, the living room, and the bedroom to predict an efficacy of the remediation for the living room, and another efficacy of the remediation for the bedroom incorporating their relative locations with the remediation device.

Aspects. It is noted that any of aspects 1-10 and 21 can be combined with any of aspects 11-20 and 22.

Aspect 1. An indoor air quality (IAQ) control system for a heating, ventilation, air conditioning, and Refrigeration (HVACR) system, comprising:

- an IAQ monitor that is configured to collect air quality data from an air quality sensor of an air quality-controlled space;
- a controller that is configured to manage a remediation device of the air quality-controlled space; and
- an IAQ management server that is configured to generate a biological pollutant estimate based on the air quality data using an algorithm that correlates the air quality data to the biological pollutant estimate, and generate a remediation recommendation based on the biological pollutant estimate.

Aspect 2. The system of aspect 1, wherein the IAQ management server is further configured to:

- control the remediation device directly or via the controller according to the remediation recommendation if the remediation recommendation can be executed by the remediation device; or
- recommend installing another remediation device appropriate for a type of pollutant being remediated if the remediation recommendation cannot be executed by the remediation device.

Aspect 3. The system of any of aspects 1-2, wherein the IAQ management server is further configured to estimate efficacy of the remediation of a biological pollutant using a rate of change of the air quality data or a change in the air quality data before and after the remediation recommendation is executed.

Aspect 4. The system of any of aspects 1-3, wherein the air quality data collected by the IAQ monitor includes a measurement of at least one of carbon dioxide, a volatile organic compound, a particulate matter, temperature, humidity, carbon monoxide, nitrogen dioxide, or sulfur dioxide.

Aspect 5. The system of any of aspects 1-4, wherein the algorithm is further configured to be updated by one or more of user feedback, a remediation response outcome, or an updated prediction model generated from empirical or simulated data.

Aspect 6. The system of any of aspects 1-5, wherein the algorithm is further configured to generate the biological pollutant estimate using ambient air quality data.

Aspect 7. The system of any of aspects 1-6, wherein the remediation device includes one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

Aspect 8. The system of aspect 7, wherein the remediation device is controllable by the controller, by a secondary controller, or by a user.

Aspect 9. The system of any of aspects 1-8, wherein the IAQ management server is further configured to deliver the remediation recommendation to a display on the controller, the IAQ monitor, or a user device.

Aspect 10. The system of any of aspects 1-9, wherein the IAQ management server is further configured to generate the remediation recommendation based on a trend in the air quality data over time.

Aspect 11. An indoor air quality (IAQ) method for a heating, ventilation, air conditioning, and refrigeration (HVACR) system, comprising:
collecting air quality data from an air quality sensor of an air quality-controlled space using an IAQ monitor;
managing a remediation device of the air quality-controlled space using a controller;
generating a biological pollutant estimate based on the air quality data using an algorithm that correlates the air quality data to the biological pollutant estimate; and
generating a remediation recommendation based on the biological pollutant estimate.

Aspect 12. The method of aspect 11, further comprising
controlling the remediation device directly or via the controller according to the remediation recommendation if the remediation recommendation can be executed by the remediation device; or
recommending installing another remediation device appropriate for a type of pollutant being remediated if the remediation recommendation cannot be executed by the remediation device.

Aspect 13. The method of any of aspects 11-12, further comprising
estimating efficacy of the remediation of a biological pollutant using a rate of change of the air quality data or a change in the air quality data before and after the remediation recommendation is executed.

Aspect 14. The method of any of aspects 11-13, wherein the air quality data collected by the IAQ monitor includes a measurement of at least one of carbon dioxide, a volatile organic compound, a particulate matter, temperature, humidity, carbon monoxide, nitrogen dioxide, or sulfur dioxide.

Aspect 15. The method of any of aspects 11-14, wherein the algorithm is configured to be updated by user feedback, a remediation response outcome, or an updated prediction model generated from empirical or simulated data.

Aspect 16. The method of any of aspects 11-15, wherein the algorithm is further configured to generate the biological pollutant estimate using ambient air quality data.

Aspect 17. The method of any of aspects 11-16, wherein the remediation device includes one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

Aspect 18. The method of aspect 17, wherein the remediation device is controllable by the controller, by a secondary controller, or by a user.

Aspect 19. The method of any of aspects 11-18, further comprising:
delivering the remediation recommendation to a display of the controller, the IAQ monitor, or a user device.

Aspect 20. The method of any of aspects 11-19, further comprising
generating the remediation recommendation based on a trend in the air quality data over time.

Aspect 21. The system of any of aspects 1-10, further comprising
a user interface of a communication device configured to deliver instructions to a user for an efficacy demonstration, wherein the instructions include directing the user to release a predetermined air pollutant into the air quality controlled space;
the controller managing the remediation device to execute a remediation action corresponding to the predetermined air pollutant;
the IAQ management server estimating an equivalent efficacy of a biological pollutant remediation using the algorithm.

Aspect 22. The method of any of aspects 11-20, further comprising
delivering instructions to a user for an efficacy demonstration through a user interface of a communication device, wherein the instructions include directing the user to release a predetermined air pollutant into the air quality controlled space;
executing a remediation action corresponding to the predetermined air pollutant;
estimating an equivalent efficacy of a biological pollutant remediation using the algorithm.

The terminology used in this Specification is intended to describe particular embodiments and is not intended to be limiting. The terms "a," "an," and "the" include the plural forms as well, unless clearly indicated otherwise. The terms "comprises" and/or "comprising," when used in this Specification, specify the presence of the stated features, integers, steps, operations, elements, and/or components, but do not preclude the presence or addition of one or more other features, integers, steps, operations, elements, and/or components.

With regard to the preceding description, it is to be understood that changes can be made in detail, especially in matters of the construction materials employed and the shape, size, and arrangement of parts without departing from the scope of the present disclosure. This Specification and the embodiments described are exemplary only, with the true scope and spirit of the disclosure being indicated by the claims that follow.

The invention claimed is:

1. An indoor air quality (IAQ) control system for a heating, ventilation, air conditioning, and refrigeration (HVACR) system, comprising:
one or more air quality sensors configured to collect air quality data of an air quality controlled space, wherein the air quality data includes one or more of carbon dioxide, a volatile organic compound, a particulate matter, temperature, humidity, carbon monoxide, nitrogen dioxide, or sulfur dioxide;
an IAQ monitor that is configured to receive the air quality data from the one or more air quality sensors of the air quality-controlled space;
one or more remediation devices in the air quality-controlled space;
a controller that is configured to control the one or more remediation devices in the air quality-controlled space;

an IAQ management server that is configured to generate a biological pollutant estimate based on the air quality data using an algorithm that correlates the air quality data to the biological pollutant estimate, and generate a remediation recommendation based on the biological pollutant estimate; and a user interface of a communication device configured to deliver instructions to a user for an efficacy demonstration, wherein:

the instructions include directing the user to release a predetermined air pollutant into the air quality controlled space;

the controller manages the remediation device to execute a remediation action corresponding to the predetermined air pollutant;

the IAQ management server estimates an equivalent efficacy of a biological pollutant remediation using the algorithm, the biological pollutant estimate is an estimate of a level of a bacterial or viral pathogen, and the controller is configured to control the one or more remediation devices based on the remediation recommendation.

2. The system of claim 1, wherein the IAQ management server is further configured to recommend installing another remediation device appropriate for a type of pollutant being remediated if the remediation recommendation cannot be executed by the remediation device.

3. The system of claim 1, wherein the IAQ management server is further configured to estimate efficacy of the remediation of a biological pollutant using a rate of change of the air quality data or a change in the air quality data before and after the remediation recommendation is executed.

4. The system of claim 1, wherein the algorithm is further configured to be updated by one or more of user feedback, a remediation response outcome, or an updated prediction model generated from empirical or simulated data.

5. The system of claim 1, wherein the algorithm is further configured to generate the biological pollutant estimate using ambient air quality data.

6. The system of claim 1, wherein the remediation device includes one or more of: a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

7. The system of claim 6, wherein the remediation device is controllable by the controller, by a secondary controller, or by a user.

8. The system of claim 1, wherein the IAQ management server is further configured to deliver the remediation recommendation to a display on the controller, the IAQ monitor, or a user device.

9. The system of claim 1, wherein the IAQ management server is further configured to generate the remediation recommendation based on a trend in the air quality data over time.

10. An indoor air quality (IAQ) method for a heating, ventilation, air conditioning, and refrigeration (HVACR) system, comprising:

collecting air quality data of an air quality controlled space using one or more air quality sensors, wherein the air quality data includes one or more of carbon dioxide, a volatile organic compound, a particulate matter, temperature, humidity, carbon monoxide, nitrogen dioxide, or sulfur dioxide;

collecting the air quality data from the one or more air quality sensors of the air quality-controlled space using an IAQ monitor;

managing a remediation device of the air quality-controlled space using a controller;

generating a biological pollutant estimate based on the air quality data using an algorithm that correlates the air quality data to the biological pollutant estimate, wherein the biological pollutant estimate is an estimate of a level of a bacterial or viral pathogen;

generating a remediation recommendation based on the biological pollutant estimate;

controlling the remediation device based on the remediation recommendations;

delivering instructions to a user for an efficacy demonstration through a user interface of a communication device, wherein the instructions include directing the user to release a predetermined air pollutant into the air quality controlled space;

executing a remediation action corresponding to the predetermined air pollutant; and estimating an equivalent efficacy of a biological pollutant remediation using the algorithm.

11. The method of claim 10, further comprising recommending installing another remediation device appropriate for a type of pollutant being remediated if the remediation recommendation cannot be executed by the remediation device.

12. The method of claim 10, further comprising estimating efficacy of the remediation of a biological pollutant using a rate of change of the air quality data or a change in the air quality data before and after the remediation recommendation is executed.

13. The method of claim 10, wherein the algorithm is configured to be updated by user feedback, a remediation response outcome, or an updated prediction model generated from empirical or simulated data.

14. The method of claim 10, wherein the algorithm is further configured to generate the biological pollutant estimate using ambient air quality data.

15. The method of claim 10, wherein the remediation device includes one or more of a smart air filter, an add-on filter monitoring device, a fan, a bipolar ionization air cleaning device, a photocatalytic air cleaning device, a stand-alone air filter unit, an aqueous or gas-phase hydrogen peroxide generator, an UV, UV-C or far UV wavelength photo source, an air quality control attachment or accessory to the HVACR system, or a door or window of the air quality controlled space.

16. The method of claim 15, wherein the remediation device is controllable by the controller, by a secondary controller, or by a user.

17. The method of claim 10, further comprising:

delivering the remediation recommendation to a display of the controller, the IAQ monitor, or a user device.

18. The method of claim 10, further comprising generating the remediation recommendation based on a trend in the air quality data over time.

* * * * *